United States Patent
Hsieh

(10) Patent No.: US 6,507,632 B1
(45) Date of Patent: Jan. 14, 2003

(54) METHOD AND APPARATUS FOR REDUCING ARTIFACTS IN AN IMAGE

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/981,063

(22) Filed: Oct. 16, 2001

(51) Int. Cl.$^7$ ................................................. A61B 6/03
(52) U.S. Cl. ............................................. 378/4; 378/15
(58) Field of Search ..................... 378/4, 8, 15, 19, 378/94

(56) References Cited

U.S. PATENT DOCUMENTS

| | | |
|---|---|---|
| 4,131,021 A | 12/1978 | Mezrich et al. |
| 4,630,203 A | 12/1986 | Szirtes |
| 4,631,750 A | 12/1986 | Gabriel et al. |
| 4,751,643 A | 6/1988 | Lorensen et al. |
| RE35,798 E | 5/1998 | Kimura |
| 6,351,514 B1 * | 2/2002 | Besson ................. 378/15 |
| 6,404,842 B1 * | 6/2002 | Hsieh ................... 378/15 |
| 6,411,670 B1 * | 6/2002 | Besson .................. 378/4 |
| 2002/0122528 A1 * | 9/2002 | Besson .................. 378/4 |

* cited by examiner

Primary Examiner—David V. Bruce
(74) Attorney, Agent, or Firm—Carl B. Horton, Esq.; Armstrong Teasdale LLP

(57) ABSTRACT

A method for reducing imaging artifacts in at least one image representative of an object with a scanning imaging system is provided. The imaging system has a multislice detector array and a radiation source configured to emit a radiation beam through the object and towards the multislice detector array. The multislice detector array has a plurality of detector elements arranged in a plurality of detector rows. The method includes scanning the object with the scanning imaging system to acquire a plurality of projection data acquired from a plurality of detector rows including two end rows and a plurality of interior detector rows. The method also includes defining a first plane of reconstruction (POR) for a particular detector row, and defining a second plane of reconstruction (POR) for the particular detector row.

33 Claims, 3 Drawing Sheets

METHOD AND APPARATUS FOR REDUCING ARTIFACTS IN AN IMAGE

BACKGROUND OF THE INVENTION

This invention relates generally to methods and apparatus for radiation imaging systems and, more particularly, to methods and apparatus for combating cone beam and helical artifacts utilizing weighted generalized helical interpolation.

In multislice computed tomographic (CT) imaging systems, a detector array is segmented so that a plurality of parallel or quasi-parallel slices of projection data are acquired and processed to construct a plurality of images corresponding to several slices though a volume. A range of pitches exists for which measurements are available at least at two source locations. Samples acquired at different source positions are known as "conjugate samples."

In some known imaging systems, using High Speed (HS) mode in which pitch values are relatively high, projection data sets do not include conjugate samples. Therefore, the cone beam and helical interpolation induced artifacts may not be effectively compensated resulting in projection images which may include image artifacts caused by helical interpolation and cone beam artifacts.

BRIEF SUMMARY OF THE INVENTION

In one aspect, a method for reducing imaging artifacts in at least one image representative of an object with a scanning imaging system is provided. The imaging system has a multislice detector array and a radiation source configured to emit a radiation beam through the object and towards the multislice detector array. The multislice detector array has a plurality of detector elements arranged in a plurality of detector rows. The method includes scanning the object with the scanning imaging system to acquire a plurality of projection data acquired from a plurality of detector rows including two end rows and a plurality of interior detector rows. The method also includes defining a first plane of reconstruction (POR) for a particular detector row, and defining a second plane of reconstruction (POR) for the particular detector row.

In another aspect, a method for reducing imaging artifacts in at least one image representative of an object with a scanning imaging system is provided. The imaging system has a multislice detector array and a radiation source configured to emit a radiation beam through the object and towards the multislice detector array. The multislice detector array has a plurality of detector elements arranged in a plurality of detector rows. The method includes scanning the object with the scanning imaging system to acquire a plurality of projection data acquired from a plurality of detector rows including two end rows and a plurality of interior detector rows. The method also includes defining a first plane of reconstruction (POR) for each detector row, and defining a second plane of reconstruction (POR) for each interior detector row. The method also includes deriving a weighting function using the first POR and the second POR.

In another aspect, a medical imaging system for estimating a material composition of an imaged object is provided. The system includes a detector array including a plurality of detector rows including two end detector rows and a plurality of interior detector rows. The system also includes at least one radiation source, and a computer coupled to the detector array and radiation source. The computer is configured to scan the object with the scanning imaging system to acquire a plurality of projection data acquired from a plurality of detector rows including two end rows and a plurality of interior detector rows. The computer is also configured to define a first plane of reconstruction (POR) for a particular detector row, and define a second plane of reconstruction (POR) for the particular detector row.

In yet another aspect, a medical imaging system for estimating a material composition of an imaged object is provided. The system includes a detector array including a plurality of detector rows including two end detector rows and a plurality of interior detector rows. The system also includes at least one radiation source, and a computer coupled to the detector array and radiation source. The computer is configured to scan the object with the scanning imaging system to acquire a plurality of projection data acquired from a plurality of detector rows including two end rows and a plurality of interior detector rows. The computer is also configured to define a first plane of reconstruction (POR) for each detector row, and define a second plane of reconstruction (POR) for each interior detector row. The computer is also configured to derive a weighting function using the first POR and the second POR.

In one aspect, a computer readable medium encoded with a program executable by a computer for reconstructing a three-dimensional dataset representative of an imaged object is provided. The program is configured to instruct the computer to scan the object with a scanning imaging system to acquire a plurality of projection data acquired from a plurality of detector rows including two end rows and a plurality of interior detector rows. The program is also configured to define a first plane of reconstruction (POR) for a particular detector row, and define a second plane of reconstruction (POR) for the particular detector row.

In another aspect, a computer readable medium encoded with a program executable by a computer for reconstructing a three-dimensional dataset representative of an imaged object is provided. The program is configured to instruct the computer to scan the object with the scanning imaging system to acquire a plurality of projection data acquired from a plurality of detector rows including two end rows and a plurality of interior detector rows. The program is also configured to define a first plane of reconstruction (POR) for each detector row, and define a second plane of reconstruction (POR) for each interior detector row. The program is also configured to derive a weighting function using the first POR and the second POR.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, passages referring to "one embodiment" of the present invention are not intended to be interpreted as excluding the existence of additional embodiments that also incorporate the recited features.

Figure 1:
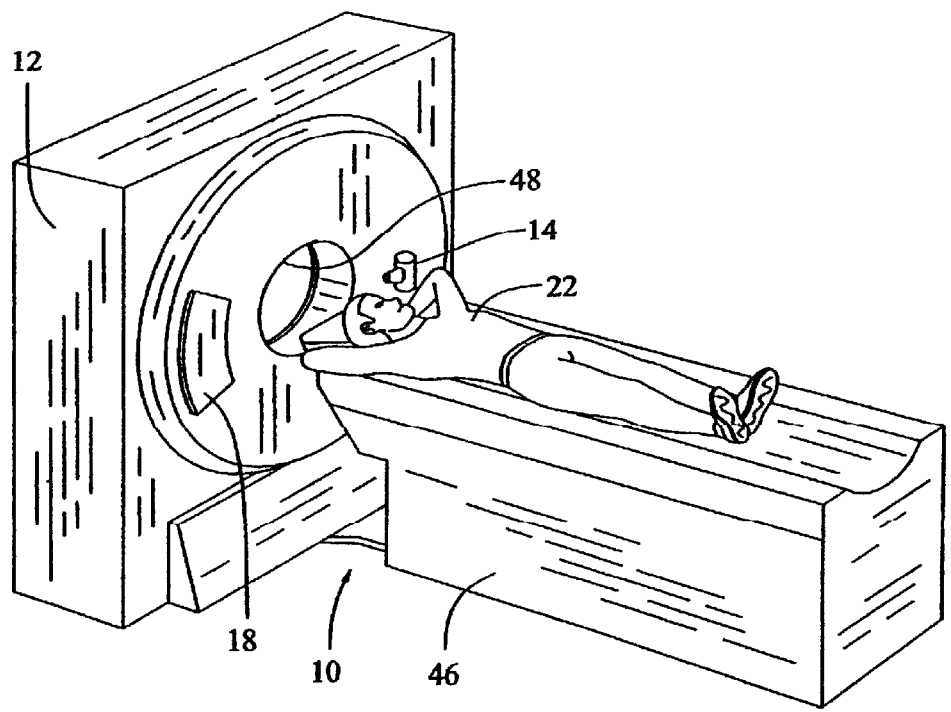
FIG. 1 is a pictorial view of a CT imaging system.
Figure 2:
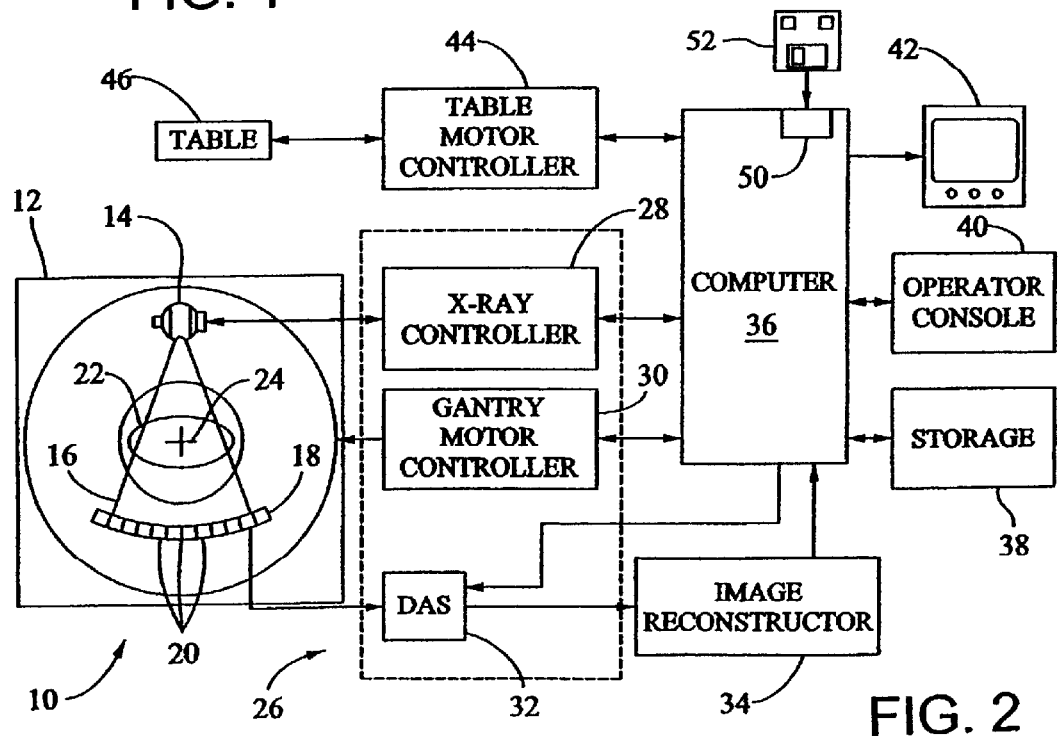
FIG. 2 is a block schematic diagram of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
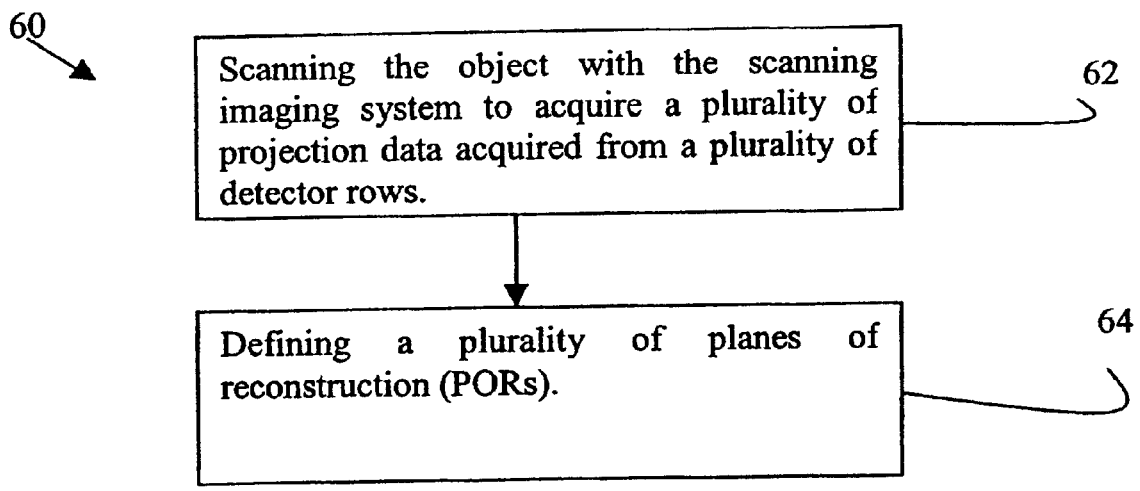
FIG. 3 is a flow diagram of a method for reducing cone beam artifacts.

FIG. 3 is a flow diagram of a method 60 for reducing imaging artifacts. Method 60 includes scanning 62 an object 22 with scanning imaging system 10 to acquire a plurality of projection data acquired from a plurality of detector rows. Method 60 also includes defining 64 a plurality of planes of reconstruction (PORs).

Figure 4:
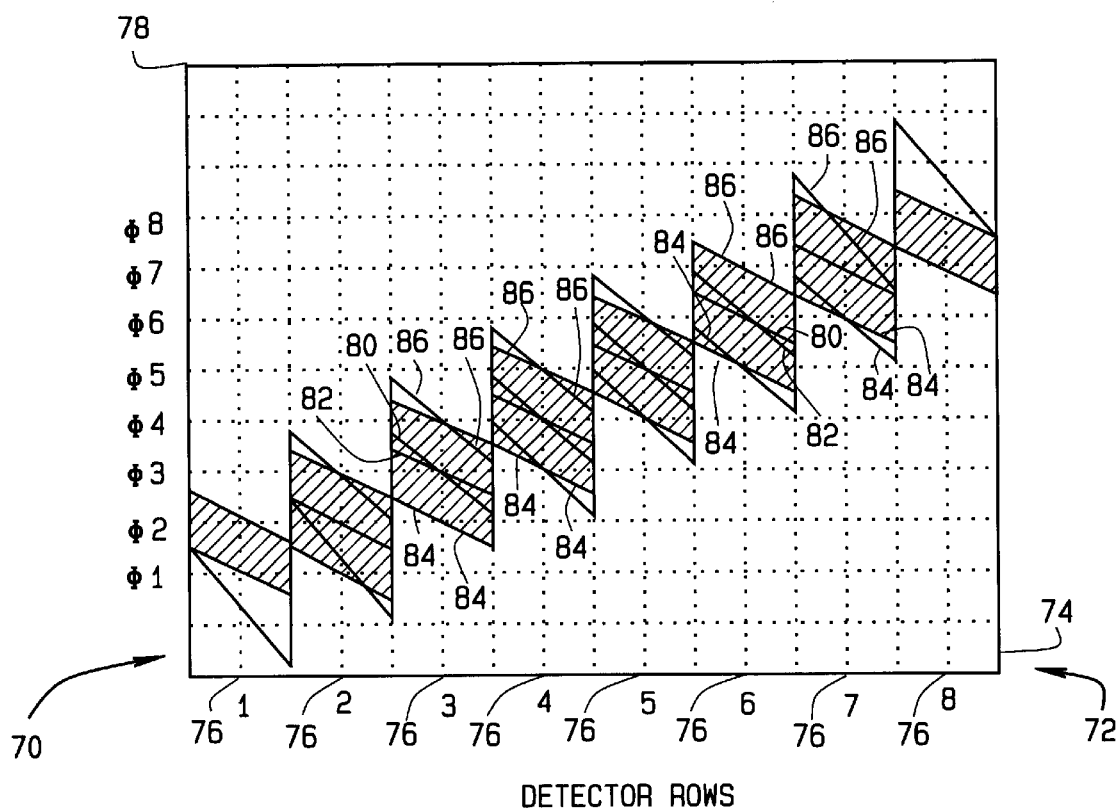
FIG. 4 is a sinogram representation of a plurality of weighting regions.

FIG. 4 is a sinogram representation of a plurality of weighting regions 70 for a plurality of detector rows 72 along a horizontal axis 74. Within each detector row 72, horizontal axis 74 represents a detector fan angle and each detector row 72 includes an iso-center 76. Figure four also includes a vertical axis 78 representing a projection view angle ($\beta$). For detector rows labeled 2–7, a plurality of planes of reconstruction (PORs) are defined. For example, detector row three includes a first plane of reconstruction (POR) 80 and a second POR 82. First POR 80 and second POR 82 intersect at iso-center 76.

In an alternative embodiment, more than two PORs are defined. A weighting function derived from more than one POR results in a smoother weighting than a weighting function derived from a single POR. Additionally, since first POR 80 and second POR 82 intersect at iso-center 76, a slice profile is impacted less near iso-center 76 and more away from iso-center 76. In other words, the impact on the slice profile is minimal near iso-center 76 and gradually increases away from iso-center 76 facilitating an accurate slice profile. Additionally, as illustrated in FIG. 4, and explained below in more detail, detector rows on the ends (the first and eighth detector rows in an eight slice detector array, "end rows") have only one POR defined and hence, samples from the first and eighth rows are used only once compared to the interior rows (2–7) in which samples are used twice or more. Because the end rows typically have worse cone angles compared to the interior rows, using one sample from the end rows facilitates reducing cone beam artifacts. Additionally, first POR 80 and second POR 82 are not co-planer, therefore at least one of first POR 80 and second POR 82 is non-parallel and non-flat to the detector row. Alternatively, first POR 80 and second POR 82 are constructed such that both first POR 80 and second POR 82 are non-parallel and non-flat to the detector row.

In use, object 22 is helically scanned with scanning imaging system 10, using a variably selected speed, such as a high speed (HS) operating mode. Imaging system 10 scans at a variably selected helical pitch (p), such as, but not limited to p=13.4:1, to collect projection data. In one embodiment, CT imaging system 10 is an eight slice CT imaging system 10. As explained below each POR is defined by a slope designated by $_{i,m,k}(\ )$ where i refers to the detector row, k refers to the number of the POR (e.g., first, second, third), and m refers to a middle and, therefore, the slope is also referred herein as the middle boundary. For example, the slope for first POR 80 of detector row 3 is designated $_{3,m,1}(\ )$, and second POR 82 of detector row 3 is designated $_{3,m,2}(\ )$. For each POR a lower boundary 84 and an upper boundary 86 for applying a weighting function are also defined. Lower boundary 84 is designated by $_{i,l,k}(\ )$ for the kth POR for the ith detector row (where l refers to lower), and upper boundary 86 is designated by $_{i,u,k}(\ )$ (where u refers to upper). Referring to detector row 3, lower boundary 84 of first POR 80 is co-linear with lower boundary 84 of second POR 82. However, lower boundary 84 of first POR 80 and lower boundary 84 of second POR 82. are not limited to being co-linear. For example, referring to detector row 6, lower boundaries 84 of first and second PORs 80 and 82 are not co-linear, rather upper boundaries 86 are co-linear. Also, referring to detector row 7, none of the boundaries 84 and 86 are co-linear.

In one embodiment, a POR (i.e., first POR 80) for the first detector row is defined by $\beta_{1,m,1}(\gamma)=\phi_1-\alpha\gamma$ (also referred to herein as a middle boundary) and the weighting function boundaries for the first detector row are defined by $\beta_{1,l,1}(\gamma)=\phi_{N-1}-\pi-(2-\alpha)\gamma$, and $\beta_{1,u,1}(\gamma)=\phi_2-\alpha\gamma$ wherein $\phi_i$ is a projection angle at which detector row i intersects the POR, N is the number of rows in the detector, $\gamma$ is a detector angle; and $\alpha$ is a parameter selected to ensure that boundary lines $\beta_{1,l,1}$ and $\beta_{1,m,1}$ do not intersect. The weighting function boundaries for the second detector row are defined by $\beta_{2,l,1}(\gamma)=\phi_N-\pi-(2-\alpha)\gamma$, $\beta_{2,m,1}(\gamma)=\beta_{1,u,1}$, and $\beta_{2,u,1}(\gamma)=\phi_3-\alpha\gamma$ $\beta_{2,l,2}(\gamma)=\beta_{1,m,1}$, $\beta_{2,m,2}(\gamma)=\beta_{2,m,1}$, and $\beta_{2,u,2}(\gamma)=\phi_3-\delta\gamma$ Where $\delta$ is a parameter to ensure that the two boundary lines $\beta_{2,m,1}$ and $\beta_{2,u,2}$ do not intersect. Parameters $\alpha$ and $\delta$ are used to force continuity of the derived weighting function. And the middle boundaries $\beta_{2,m,1}$ and $\beta_{2,m,2}$ define the PORs for the second detector row. As used herein, all middle boundaries $\beta_{n,m,k}$ define the kth POR for the nth detector row.

The weighting function boundaries for detector rows n where (2<n<N-1) are defined by $\beta_{n,l,1}(\gamma)=\beta_{n-1,m,1}$, $\beta_{n,m,1}(\gamma)=\beta_{n-1,m,1}$, and $\beta_{n,u,1}(\gamma)=\phi_{n+1}-\alpha\gamma$ $\beta_{n,l,2}(\gamma)=\beta_{n-1,m,2}$, $\beta_{n,m,2}(\gamma)=\beta_{n-1,u,2}$, and $\beta_{n,u,2}(\gamma)=\phi_{n+1}-\delta\gamma$ The parameters $\alpha$ and $\delta$ are not equal to ensure multiple PORs.

The weighting function boundaries for detector row N-1 (in an eight slice embodiment, the seventh detector row) are defined by $\beta_{N-1,l,1}(\gamma)=\beta_{N-2,m,1}$, $\beta_{N-1,m,1}(\gamma)=\beta_{N-2,u,1}$, and $\beta_{N-1,u,1}(\gamma)=\phi_1+\pi-(2-\alpha)\gamma$ $\beta_{N-1,l,2}(\gamma)=\beta_{N-2,m,2}$, $\beta_{N-1,m,2}(\gamma)=\beta_{N-1,m,1}$, and $\beta_{N-1,u,2}(\gamma)=\phi_N-\alpha\gamma$ The weighting function boundaries for the Nth detector row (eighth detector row) are defined by $\beta_{N,l,1}(\gamma)=\beta_{N-1,m,1}$, $\beta_{N,m,1}(\gamma)=\phi_N-\alpha\gamma$, and $\beta_{N,u,1}(\gamma)=\phi_2+\pi-(2-\alpha)\gamma$ A helical weighting function $(w_{n,k}(\gamma,\beta))$ can be derived using the upper, middle and lower boundaries for a plurality of detector row regions. The weighting function can be calculated according to:

$$w_{n,k}(\gamma,\beta) = \begin{cases} \frac{\beta - \beta_{n,l,k}(\gamma)}{\beta_{n,m,k}(\gamma) - \beta_{n,l,k}(\gamma)}, & \beta_{n,l,k}(\gamma) \leq \beta < \beta_{n,m,k}(\gamma) \\ \frac{\beta_{n,u,k}(\gamma) - \beta}{\beta_{n,u,k}(\gamma) - \beta_{n,m,k}(\gamma)}, & \beta_{n,m,k}(\gamma) \leq \beta < \beta_{n,u,k}(\gamma) \\ 0, \end{cases}$$

otherwise

In one embodiment, a helical weight for each detector row, $w_n(\gamma,\beta)$, is a summation over k, i.e., $w_n(\gamma,\beta)=w_{n,1}(\gamma,\beta)+w_{n,2}(\gamma,\beta)$ When more than two PORs are selected, additional scaling factor can be used to ensure overall contribution of weights remains the same. For example, if four PORs are selected, a scaling factor of 0.5 is used so that $$w_n(\gamma, \beta) = 0.5 \sum_{k=1}^{4} w_{n,k}(\gamma, \beta).$$

The projection data set is multiplied by the weighting function on a row by row basis. The weighted projections are then summed over all rows on a view by view basis. Filtered backprojection operation is then performed on the summed projections. In one embodiment, the defined boundaries are straight lines. In another embodiment, the boundaries are non-linear or piece-wise linear. Using non-linear lines facilitates flexibility in the selection of the parameters $\alpha$ and $\delta$.

In one embodiment, and as described herein, two sets of boundaries are defined for each interior detector row (k=1, and k=2). In a further embodiment, multiple (e.g., k=1, 2, 3, or 4) sets of boundaries can be used to form the final weight function. The weighting function derived from each boundary set can be summed with equality as shown herein.

Other embodiments of the present invention include apparatus described above as scanning imaging system 10. The imaging system is configured to perform one or more of the methods described above using, for example, image reconstructor 34 to receive sampled and digitized projection views and computer 36 which stores the image in a mass storage device 38. An associated display 42, such as a cathode ray tube and a liquid crystal display, allows the operator to observe the reconstructed image. In one embodiment, firmware and/or software is configured to instruct either or both of image reconstructor 34 and/or computer 36 to control imaging system 10 to perform one or more of the method embodiments described above.

It is possible to reconstruct images of an object 22 after scanning (e.g., at a later date), on a processor 36 separate from imaging system 10. Some of these embodiments are similar to the scanning imaging system embodiments described above, but differ in that hardware, software and/or firmware is not necessarily provided to perform a helical scan to collect projection data. In one embodiment, a processor comprises at least a computer 36, which may be, but is not necessarily part of imaging system 10. The processor may also comprise a separate image reconstructor 34. The processor is configured to accept as input a plurality of projection views of a scanned object. The projection views include projection views acquired at different cone angles of a radiation beam by a multislice detector array having a plurality of detector rows. The processor is configured to select a region of reconstruction to define sets of conjugate samples in the projection views, and to reconstruct at least one image of the object. To reconstruct the image, the processor is configured to weight sets samples, and to filter and backproject the weighted samples. In yet another embodiment, a computer readable medium (e.g., a floppy disk or a CD-ROM) is provided that has instructions interpretable by a computer or processor 36 to instruct it to perform these steps.

Embodiments of the present invention provide increased coverage while maintaining high image quality. In particular, at least one embodiment of the present invention produces high quality images from projection views acquired from an eight-slice detector array at a pitch of 13.4:1.

While the invention has been described in terms of various specific embodiments, those skilled in the art will recognize that the invention can be practiced with modification within the spirit and scope of the claims.

What is claimed is:

1. A method for reducing imaging artifacts in at least one image representative of an object with a scanning imaging system having a multislice detector array and a radiation source configured to emit a radiation beam through the object and towards the multislice detector array, the multislice detector array having a plurality of detector elements arranged in a plurality of detector rows, said method comprising:

scanning the object with the scanning imaging system to acquire a plurality of projection data acquired from a plurality of detector rows including two end rows and a plurality of interior detector rows;

defining a first plane of reconstruction (POR) for a particular detector row; and defining a second plane of reconstruction (POR) for the particular detector row.

2. A method in accordance with claim 1 wherein defining a first plane of reconstruction comprises defining a first plane of reconstruction for each detector row, defining a second plane of reconstruction comprises defining a second plane of reconstruction for each interior detector row.

3. A method in accordance with claim 1 wherein defining a first plane of reconstruction for a particular detector row comprises defining a first plane of reconstruction for a particular detector row according to $$\beta_{n,m,1}(\gamma)=\phi_n-\alpha\gamma.$$

wherein n is the detector row number;

$\phi_n$ is a projection angle at which detector row n intersects the plane of reconstruction (POR);

$\gamma$ is a detector angle; and $\alpha$ is a parameter.

4. A method in accordance with claim 2 wherein a is selected such that boundary line $\beta_{n,m,1}$ does not intersect a lower boundary $\beta_{n,l,1}$ of a weighting function.

5. A method in accordance with claim 1 wherein defining a second plane of reconstruction for the particular detector row comprises defining a second plane of reconstruction for the particular detector row according to $$\beta_{n,m,2}(\gamma)=\phi_n-\delta\gamma$$

wherein n is the detector row number;

$\phi_n$ is a projection angle at which detector row n intersects the plane of reconstruction (POR);

$\gamma$ is a detector angle; and $\delta$ is a parameter.

6. A method in accordance with claim 5 wherein $\delta$ is selected such that boundary line $\beta_{n,m,2}$ does not intersect an upper boundary $\beta_{n,u,2}$ of a weighting function.

7. A method in accordance with claim 1 further comprising deriving a weighting function using the first POR and the second POR.

8. A method in accordance with claim 7 wherein deriving a weighting function comprises deriving a weighting function according to:

$$w_{n,k}(\gamma,\beta)=\begin{cases}\dfrac{\beta-\beta_{n,l,k}(\gamma)}{\beta_{n,m,k}(\gamma)-\beta_{n,l,k}(\gamma)},&\beta_{n,l,k}(\gamma)\leq\beta<\beta_{n,m,k}(\gamma)\\ \dfrac{\beta_{n,u,k}(\gamma)-\beta}{\beta_{n,u,k}(\gamma)-\beta_{n,m,k}(\gamma)},&\beta_{n,m,k}(\gamma)\leq\beta<\beta_{n,u,k}(\gamma)\\ 0,\end{cases}$$

otherwise wherein n is the detector row number;

l designates a lower boundary;

m designates a middle boundary;

u designates an upper boundary; and $\gamma$ is a detector angle.

9. A method in accordance with claim 8 further comprising summing and scaling $w_{n,k}(\gamma,\beta)$ over k to obtain a final weight.

10. A method in accordance with claim 8 wherein:

$$\beta_{1,l,1}(\gamma)=\phi_{N-1}-\pi-(2-\alpha)\gamma,\beta_{1,u,1}(\gamma)=\phi_2-\alpha\gamma;$$

$$\beta_{2,l,1}(\gamma)=\phi_N-\pi-(2-\alpha)\gamma,\beta_{2,m,1}(\gamma)=\beta_{1,u,1},\beta_{2,u,1}(\gamma)=\phi_3-\alpha\gamma;$$

$$\beta_{2,l,2}(\gamma)=\beta_{1,m,1},\beta_{2,m,2}(\gamma)=\beta_{2,m,1},\beta_{2,u,2}(\gamma)=\phi_3-\delta\gamma;$$

$$\beta_{n,l,1}(\gamma)=\beta_{n-1,m,1},\beta_{n,m,1}(\gamma)=\beta_{n-1,u,1},\beta_{n,u,1}(\gamma)=\phi_{n+1}-\alpha\gamma\text{ for }2<n<N-1;$$

$$\beta_{n,l,2}(\gamma)=\beta_{n-1,m,2},\beta_{n,m,2}(\gamma)=\beta_{n-1,u,2},\beta_{n,u,2}(\gamma)=\phi_{n+1}-\delta\gamma\text{ for }2<n<N-1;$$

$$\beta_{N-1,l,1}(\gamma)=\beta_{N-2,m,1},\beta_{N-1,m,1}(\gamma)=\beta_{N-2,u,1},\beta_{N-1,u,1}(\gamma)=\phi_1+\pi-(2-\alpha)\gamma;$$

$$\beta_{N-1,l,2}(\gamma)=\beta_{N-2,m,2},\beta_{N-1,m,2}(\gamma)=\beta_{N-1,m,1},\beta_{N-1,u,2}(\gamma)=\phi_N-\alpha\gamma;\text{ and}$$

$$\beta_{N,l,1}(\gamma)=\beta_{N-1,m,1},\beta_{N,m,1}(\gamma)=\phi_N-\alpha\gamma,\beta_{N,u,1}(\gamma)=\phi_2+\pi-(2-\alpha)\gamma$$

wherein N is the number of detector rows, $\phi_n$ is a projection angle at which detector row n intersects the plane of reconstruction (POR), and $\delta$ and $\alpha$ are parameters.

11. A method for reducing imaging artifacts in at least one image representative of an object with a scanning imaging system having a multislice detector array and a radiation source configured to emit a radiation beam through the object and towards the multislice detector array, the multislice detector array having a plurality of detector elements arranged in a plurality of detector rows, said method comprising:

scanning the object with the scanning imaging system to acquire a plurality of projection data acquired from a plurality of detector rows including two end rows and a plurality of interior detector rows;

defining a first plane of reconstruction (POR) for each detector row;

defining a second plane of reconstruction (POR) for each interior detector row; and deriving a weighting function using the first POR and the second POR.

12. A medical imaging system for estimating a material composition of an imaged object, said medical imaging system comprising:

a detector array comprising a plurality of detector rows comprising two end detector rows and a plurality of interior detector rows;

at least one radiation source; and a computer coupled to said detector array and radiation source and configured to:

scan the object with the scanning imaging system to acquire a plurality of projection data acquired from a plurality of detector rows including two end rows and a plurality of interior detector rows;

define a first plane of reconstruction (POR) for a particular detector row; and define a second plane of reconstruction (POR) for the particular detector row.

13. A medical imaging system in accordance with claim 12 wherein said computer further configured to:

define a first plane of reconstruction for each detector row; and define a second plane of reconstruction for each interior detector row.

14. A medical imaging system in accordance with claim 12 wherein said computer further configured to define a first plane of reconstruction for a particular detector row according to $$\beta_{n,m,1}(\gamma)=\phi_n-\alpha\gamma.$$

wherein
   n is the number of the detector row;
   $\phi_n$ is a projection angle at which detector row n intersects the plane of reconstruction (POR);
   $\gamma$ is a detector angle; and
   $\alpha$ is a parameter.

15. A medical imaging system in accordance with claim 12 wherein said computer further configured to define a first plane of reconstruction for a particular detector row according to $$\beta_{n,m,1}(\gamma)=\phi_n-\alpha\gamma.$$

wherein
   n is the number of the detector row;
   $\phi_n$ is a projection angle at which detector row n intersects the plane of reconstruction (POR);
   $\gamma$ is a detector angle; and
   $\alpha$ is a parameter such that boundary line $\beta_{n,m,1}$ does not intersect a lower boundary $\beta_{n,l,1}$ of a weighting function.

16. A medical imaging system in accordance with claim 12 wherein said computer further configured to define a second plane of reconstruction for the particular detector row according to $$\beta_{n,m,2}(\gamma)=\phi_n-\delta\gamma$$

wherein
   n is the detector row number;
   $\phi_n$ is a projection angle at which detector row n intersects the plane of reconstruction (POR);
   $\gamma$ is a detector angle; and
   $\delta$ is a parameter.

17. A medical imaging system in accordance with claim 12 wherein said computer further configured to define a second plane of reconstruction for the particular detector row according to $$\beta_{n,m,2}(\gamma)=\phi_n-\delta\gamma$$

wherein
   n is the detector row number;
   $\phi_n$ is a projection angle at which detector row n intersects the plane of reconstruction (POR);
   $\gamma$ is a detector angle; and
   $\delta$ is a parameter such that boundary line $\beta_{n,m,2}$ does not intersect an upper boundary $\beta_{n,u,2}$ of a weighting function.

18. A medical imaging system in accordance with claim 12 wherein said computer further configured to derive a weighting function using the first POR and the second POR.

19. A medical imaging system in accordance with claim 12 wherein said computer further configured to derive a weighting function using the first POR and the second POR according to:

$$w_{n,k}(\gamma,\beta) = \begin{cases} \dfrac{\beta-\beta_{n,l,k}(\gamma)}{\beta_{n,m,k}(\gamma)-\beta_{n,l,k}(\gamma)}, & \beta_{n,l,k}(\gamma) \le \beta < \beta_{n,m,k}(\gamma) \\ \dfrac{\beta_{n,u,k}(\gamma)-\beta}{\beta_{n,u,k}(\gamma)-\beta_{n,m,k}(\gamma)}, & \beta_{n,m,k}(\gamma) \le \beta < \beta_{n,u,k}(\gamma) \\ 0, & \text{otherwise} \end{cases}$$

wherein
   n is the detector row number;
   l designates a lower boundary;
   m designates a middle boundary;
   u designates an upper boundary; and
   $\gamma$ is a detector angle.

20. A medical imaging system in accordance with claim 19 wherein said computer further configured to sum and scale $w_{n,k}(\gamma,\beta)$ over k to obtain a final weight.

21. A medical imaging system in accordance with claim 19 wherein:

$$\beta_{1,l,1}(\gamma)=\phi_{N-1}-\pi-(2-\alpha)\gamma, \beta_{1,u,1}(\gamma)=\phi_2-\alpha\gamma;$$

$$\beta_{2,l,1}(\gamma)=\phi_N-\pi-(2-\alpha)\gamma, \beta_{2,m,1}(\gamma)=\beta_{1,u,1}, \beta_{2,u,1}(\gamma)=\phi_3-\alpha\gamma;$$

$$\beta_{2,l,2}(\gamma)=\beta_{1,m,1}, \beta_{2,m,2}(\gamma)=\beta_{2,m,1}, \beta_{2,u,2}(\gamma)=\phi_3-\delta\gamma;$$

$$\beta_{n,l,1}(\gamma)=\beta_{n-1,m,1}, \beta_{n,m,1}(\gamma)=\beta_{n-1,u,1}, \beta_{n,u,1}(\gamma)=\phi_{n+1}-\alpha\gamma \text{ for } 2<n<N-1;$$

$$\beta_{n,l,2}(\gamma)=\beta_{n-1,m,2}, \beta_{n,m,2}(\gamma)=\beta_{n-1,u,2}, \beta_{n,u,2}(\gamma)=\phi_{n+1}-\delta\gamma \text{ for } 2<n<N-1;$$

$$\beta_{N-1,l,1}(\gamma)=\beta_{N-2,m,1}, \beta_{N-1,m,1}(\gamma)=\beta_{N-2,u,1}, \beta_{N-1,u,1}(\gamma)=\phi_1+\pi-(2-\alpha)\gamma;$$

$$\beta_{N-1,l,2}(\gamma)=\beta_{N-2,m,2}, \beta_{N-1,m,2}(\gamma)=\beta_{N-1,m,1}, \beta_{N-1,u,2}(\gamma)=\phi_N-\alpha\gamma; \text{ and}$$

$$\beta_{N,l,1}(\gamma)=^\circ\beta_{N-1,m,1}, \beta_{N,m,1}(\gamma)=\phi_N-\alpha\gamma, \beta_{N,u,1}(\gamma)=\phi_2+\pi-(2-\alpha)\gamma$$

wherein N is the number of detector rows, $\phi_n$ is a projection angle at which detector row n intersects the plane of reconstruction (POR), and $\delta$ and $\alpha$ are parameters.

22. A medical imaging system for estimating a material composition of an imaged object, said medical imaging system comprising:
   a detector array comprising a plurality of detector rows comprising two end detector rows and a plurality of interior detector rows;
   at least one radiation source; and
   a computer coupled to said detector array and radiation source and configured to:
      scan the object with the scanning imaging system to acquire a plurality of projection data acquired from a plurality of detector rows including two end rows and a plurality of interior detector rows;
      define a first plane of reconstruction (POR) for each detector row;
      define a second plane of reconstruction (POR) for each interior detector row; and
      derive a weighting function using the first POR and the second POR.

23. A computer readable medium encoded with a program executable by a computer for reconstructing a three-dimensional dataset representative of an imaged object, said program configured to instruct the computer to:
   scan the object with a scanning imaging system to acquire a plurality of projection data acquired from a plurality of detector rows including two end rows and a plurality of interior detector rows;
   define a first plane of reconstruction (POR) for a particular detector row; and
   define a second plane of reconstruction (POR) for the particular detector row.

24. A computer readable medium in accordance with claim 21 wherein said program further configured to instruct the computer to:
   define a first plane of reconstruction for each detector row; and
   define a second plane of reconstruction for each interior detector row.

25. A computer readable medium in accordance with claim 23 wherein said program further configured to instruct the computer to define a first plane of reconstruction for a particular detector row according to $$\beta_{n,m,1}(\gamma)=\phi_n-\alpha\gamma$$

wherein n is the number of the detector row;

$\phi_n$ is a projection angle at which detector row n intersects the plane of reconstruction (POR);

γ is a detector angle; and

α is a parameter.

26. A computer readable medium in accordance with claim 23 wherein said program further configured to instruct the computer to define a first plane of reconstruction for a particular detector row according to $$\beta_{n,m,1}(\gamma)=\phi_n-\alpha\gamma.$$

wherein n is the number of the detector row;

$\phi_n$ is a projection angle at which detector row n intersects the plane of reconstruction (POR);

γ is a detector angle; and

α is a parameter such that boundary line $\beta_{n,m,1}$ does not intersect a lower boundary $\beta_{n,l,1}$ of a weighting function.

27. A computer readable medium in accordance with claim 23 wherein program further configured to instruct the computer to define a second plane of reconstruction for the particular detector row according to $$\beta_{n,m,2}(\gamma)=\phi_n-\delta\gamma$$

wherein n is the detector row number;

$\phi_n$ is a projection angle at which detector row n intersects the plane of reconstruction (POR);

γ is a detector angle; and

δ is a parameter.

28. A computer readable medium in accordance with claim 23 wherein program further configured to instruct the computer to define a second plane of reconstruction for the particular detector row according to $$\beta_{n,m,2}(\gamma)=\phi_n-\delta\gamma$$

whβ2,m,1erein n is the detector row number;

$\phi_n$ is a projection angle at which detector row n intersects the plane of reconstruction (POR);

γ is a detector angle; and

δ is a parameter such that boundary line $\beta_{n,m,2}$ does not intersect an upper boundary $\beta_{n,u,2}$ of a weighting function.

29. A computer readable medium in accordance with claim 23 wherein program further configured to instruct the computer to derive a weighting function using the first POR and the second POR.

30. A computer readable medium in accordance with claim 23 wherein program further configured to derive a weighting function using the first POR and the second POR according to:

$$w_{n,k}(\gamma,\beta) = \begin{cases} \dfrac{\beta - \beta_{n,l,k}(\gamma)}{\beta_{n,m,k}(\gamma) - \beta_{n,l,k}(\gamma)}, & \beta_{n,l,k}(\gamma) \leq \beta < \beta_{n,m,k}(\gamma) \\ \dfrac{\beta_{n,u,k}(\gamma) - \beta}{\beta_{n,u,k}(\gamma) - \beta_{n,m,k}(\gamma)}, & \beta_{n,m,k}(\gamma) \leq \beta < \beta_{n,u,k}(\gamma) \\ 0, \end{cases}$$

otherwise wherein n is the detector row number;

l designates a lower boundary;

m designates a middle boundary;

u designates an upper boundary; and

γ is a detector angle.

31. A computer readable medium in accordance with claim 28 wherein program further configured to instruct the computer to sum and scale $w_{n,k}(\gamma,\beta)$ over k to obtain a final weight.

32. A computer readable medium in accordance with claim 30 wherein:

$$\beta_{1,l,1}(\gamma)=\phi_{N-1}-\pi-(2-\alpha)\gamma,\beta_{1,u,1}(\gamma)=\phi_2-\alpha\gamma;$$

$$\beta_{2,l,1}(\gamma)=\phi_N-\pi-(2-\alpha)\gamma,\beta_{2,m,1}(\gamma)=\beta_{1,u,1},\beta_{2,u,1}(\gamma)=\phi_3-\alpha\gamma;$$

$$\beta_{2,l,2}(\gamma)=\beta_{1,m,1},\beta_{2,m,2}(\gamma)=\beta_{2,m,1},\beta_{2,u,2}(\gamma)=\phi_3-\delta\gamma;$$

$$\beta_{n,l,1}(\gamma)=\beta_{n-1,m,1},\beta_{n,m,1}(\gamma)=\beta_{n-1,u,1},\beta_{n,u,1}(\gamma)=\phi_{n+1}-\alpha\gamma \text{ for } 2<n<N-1;$$

$$\beta_{n,l,2}(\gamma)=\beta_{n-1,m,2},\beta_{n,m,2}(\gamma)=\beta_{n-1,u,2},\beta_{n,u,2}(\gamma)=\phi_{n+1}-\delta\gamma \text{ for } 2<n<N-1;$$

$$\beta_{N-1,l,1}(\gamma)=\beta_{N-2,m,1},\beta_{N-1,m,1}(\gamma)=\beta_{N-2,u,1},\beta_{N-1,u,1}(\gamma)=\phi_1+\pi-(2-\alpha)\gamma;$$

$$\beta_{N-1,l,2}(\gamma)=\beta_{N-2,m,2},\beta_{N-1,m,2}(\gamma)=\beta_{N-1,m,1},\beta_{N-1,u,2}(\gamma)=\phi_N-\alpha\gamma; \text{ and}$$

$$\beta_{N,l,1}(\gamma)=\beta_{N-1,m,1},\beta_{N,m,1}(\gamma)=\phi_N-\alpha\gamma,\beta_{N,u,1}(\gamma)=\phi_2+\pi-(2-\alpha)\gamma$$

wherein N is the number of detector rows, $\phi_n$ is a projection angle at which detector row n intersects the plane of reconstruction (POR), and δ and α are parameters.

33. A computer readable medium encoded with a program executable by a computer for reconstructing a three-dimensional dataset representative of an imaged object, said program configured to instruct the computer to:

scan the object with the scanning imaging system to acquire a plurality of projection data acquired from a plurality of detector rows including two end rows and a plurality of interior detector rows;

define a first plane of reconstruction (POR) for each detector row;

define a second plane of reconstruction (POR) for each interior detector row; and derive a weighting function using the first POR and the second POR.

* * * * *

UNITED STATES PATENT AND TRADEMARK OFFICE
CERTIFICATE OF CORRECTION

PATENT NO.   : 6,507,632 B1
DATED        : January 14, 2003
INVENTOR(S)  : Hsieh It is certified that error appears in the above-identified patent and that said Letters Patent is hereby corrected as shown below:

Column 5,
Line 19, delete "$\beta_{n-1,m,1}$,and" and insert therefor -- $\beta_{n-1,u,1}$,and --.

Column 8,
Line 14, insert a comma -- , -- between "$\beta_{N-2,m,2}$" and "$\beta_{N-1,m,2}(\gamma)$".

Column 10,
Line 24, delete "º".

Column 11,
Line 50, delete "wh$\beta$2,m,1erein" and insert therefor -- wherein --.

Column 12,
Line 30, insert a comma -- , -- between "$\beta_{1,u,1}$" and "$\beta_{2,u,1}(\gamma)$".

Signed and Sealed this

Twenty-second Day of July, 2003

JAMES E. ROGAN
*Director of the United States Patent and Trademark Office*